United States Patent
Schroeder et al.

(10) Patent No.: US 9,937,009 B2
(45) Date of Patent: Apr. 10, 2018

(54) TORQUE-LIMITING ASSEMBLY FOR A SURGICAL POWERTOOL

(75) Inventors: Stephan Schroeder, Hannover (DE); Kevin Soldan, Solothurn (CH)

(73) Assignee: Stryker European Holdings I, LLC, Kalamazoo, MI (US)

( * ) Notice: Subject to any disclaimer, the term of this patent is extended or adjusted under 35 U.S.C. 154(b) by 402 days.

(21) Appl. No.: 14/387,333

(22) PCT Filed: Mar. 30, 2012

(86) PCT No.: PCT/EP2012/001425
§ 371 (c)(1),
(2), (4) Date: Jan. 5, 2015

(87) PCT Pub. No.: WO2013/143563
PCT Pub. Date: Oct. 3, 2013

(65) Prior Publication Data
US 2015/0148176 A1 May 28, 2015

(51) Int. Cl.
*A61B 17/66* (2006.01)
*A61B 17/88* (2006.01)
(Continued)

(52) U.S. Cl.
CPC .......... *A61B 19/30* (2013.01); *A61B 17/1622* (2013.01); *A61B 17/1624* (2013.01); *A61B 17/8875* (2013.01); *A61B 90/03* (2016.02); *A61C 1/186* (2013.01); *F16D 9/10* (2013.01); *A61B 2017/00482* (2013.01); *A61B 2090/031* (2016.02); *A61B 2090/037* (2016.02)

(58) Field of Classification Search
None
See application file for complete search history.

(56) References Cited

U.S. PATENT DOCUMENTS 2,130,111 A    9/1938  Whitney et al.
2,566,211 A *  8/1951  Keesling ............ A61B 17/1624
                                                475/270
(Continued)

FOREIGN PATENT DOCUMENTS

DE        3143148 A1    5/1982
DE     202007010665 U1  12/2007
(Continued)

OTHER PUBLICATIONS

International Search Report for PCT/EP/2012/001425 dated Feb. 27, 2013.

*Primary Examiner* — Robert W Hodge
*Assistant Examiner* — Ryan P Dodd
(74) *Attorney, Agent, or Firm* — Lerner, David, Littenberg, Krumholz & Mentlik, LLP (57) ABSTRACT

A torque-limiting assembly for a surgical powertool has an input shaft and an output shaft. Two relatively rotatable parts of the assembly are configured to be locked against relative rotation by at least one shearable piece for torque transfer between the input shaft and the output shaft up to a torque limit. The assembly further comprises at least one shear off structure rotationally fixed to one of the two relatively rotatable parts for shearing off a portion of the at least one shearable piece above the torque limit so as to unlock the two relatively rotatable parts for relative rotation.

17 Claims, 9 Drawing Sheets

(51) Int. Cl.
*A61B 19/00* (2006.01)
*A61B 17/16* (2006.01)
*A61C 1/18* (2006.01)
*F16D 9/10* (2006.01)
*A61B 90/00* (2016.01)
*A61B 17/00* (2006.01)

(56) References Cited

U.S. PATENT DOCUMENTS

| | | | |
|---|---|---|---|
| 3,779,105 | A | 12/1973 | Triplett et al. |
| 4,199,963 | A * | 4/1980 | van der Lely ............ F16D 9/10 464/33 |
| 4,292,819 | A * | 10/1981 | van der Lely ....... A01B 61/025 464/33 |
| 4,472,985 | A | 9/1984 | Orikasa |
| 6,139,228 | A | 10/2000 | Longo |
| 7,296,500 | B1 | 11/2007 | Martinelli |
| 8,028,608 | B2 * | 10/2011 | Sixto, Jr. .............. A61B 17/888 606/104 |
| 2001/0004610 | A1 | 6/2001 | Casutt |
| 2003/0100398 | A1 * | 5/2003 | McKay ................... B64C 13/24 475/263 |
| 2004/0138662 | A1 * | 7/2004 | Landry .............. A61B 17/1604 606/86 A |

FOREIGN PATENT DOCUMENTS

| | | |
|---|---|---|
| EP | 1880802 A2 | 1/2008 |
| WO | 0139930 A1 | 6/2001 |

* cited by examiner

TORQUE-LIMITING ASSEMBLY FOR A SURGICAL POWERTOOL

CROSS-REFERENCE TO RELATED APPLICATIONS

The present application is a national phase entry under 35 U.S.C. § 371 of International Application No. PCT/EP2012/001425 filed Mar. 30, 2012, published in English as WO 2013/143563 A1, the disclosure of which is hereby incorporated herein by reference.

TECHNICAL FIELD

The present disclosure generally relates to a surgical powertool for use in surgical procedures. In particular, a torque-limiting assembly for a surgical powertool and a system comprising the torque-limiting assembly are described.

BACKGROUND

When treating a bone fracture, bone fragments are typically aligned in a first step. The aligned bone fragments may then be fixed by a bone plate having multiple through openings. Bone screws are screwed through the bone plate openings into the bone fragments using a surgical powertool driving a screw driver blade.

To prevent damage of bone screws or similar implants and the screw driver blade, a powertool with a torque-limiting function may be used. The torque-limiting function may be realized mechanically or electronically. Conventional powertools with an electronic torque-limiter often exceed the set target torque. Such torque overshooting is highly undesirable when screwing a bone screw into bone since the bone screw, the bone or the powertool may be damaged. Also mechanical torque-limiters have such drawbacks.

A torque-limiting function may be integrated as an assembly with the powertool or implemented as a separate, dedicated torque-limiter. When using the latter, the surgical procedure is complicated by additional steps: engaging the first few threads by hand or with a screwdriver, inserting the screw further with the powertool until only a few threads are remaining and final tightening by hand, using the dedicated torque-limiter.

Additionally, due to the fact that different bone screws may be dimensioned for different torques, a surgical procedure with conventional torque-limiting powertools is time consuming since the surgeon needs to manually adjust the target torque for each bone screw. Moreover, a surgical procedure using a powertool with a conventional target torque setting is vulnerable to the human factor and a bone screw may be tightened with a wrongly designated torque.

SUMMARY

Accordingly, there is a need for a reliable torque-limiting assembly for a surgical powertool.

According to one aspect, a torque-limiting assembly for a surgical powertool is provided, wherein the assembly comprises an input shaft and an output shaft, wherein two relatively rotatable parts of the assembly are configured to be locked against relative rotation by at least one shearable piece for torque transfer between the input shaft and the output shaft up to a torque limit, and wherein the assembly further comprises at least one shear off structure rotationally fixed to one of the two relatively rotatable parts for shearing off a portion of the at least one shearable piece above the torque limit so as to unlock the two relatively rotatable parts for relative rotation.

The torque-limiting assembly may further comprise a planetary or any other type of gearing arranged between the input shaft and the output shaft. The gearing may have a certain gear ratio (e.g., a gear ratio selected such that a speed of the input shaft is reduced and an output torque is increased).

In the case of a planetary gearing, the input shaft may be connected to a sun gear or a planet gear carrier thereof. The output shaft may be connected to the sun gear when the input shaft is connected to the planet gear carrier. Alternatively, the output shaft may be connected to the planet gear carrier when the input shaft is connected to the sun gear. The planetary gearing may further comprise a ring gear.

The two relatively rotatable parts may include a stationary part of the torque-limiting assembly and a part of the gearing such as, in the case of a planetary gearing, the ring gear or a part rotationally fixed to the ring gear. Alternatively, the two relatively rotatable parts may include a stationary part of the torque-limiting assembly and the planet carrier or a part rotationally fixed to the planet carrier. The stationary part may be a housing of the torque-limiting assembly or a part rotationally fixed to the housing.

The shear off structure may be rotationally fixed to the ring gear of the planetary gear or to the part rotationally fixed to the ring gear for shearing off a portion of the at least one shearable piece. The shear off structure may constitute a part of the ring gear. The shear off structure may be realized as a recess in the ring gear or in a part rotationally fixed to the ring gear. As an example, the shear off structure may be configured as a surface of the ring gear or of a part rotationally fixed to the ring gear. The surface may extend in the radial and/or longitudinal direction of the ring gear.

The torque-limiting assembly may further comprise a locking member for rotationally locking the two relatively rotatable parts above the torque limit. The locking member may be L-shaped. That is, the locking member may have a second portion extending in a direction substantially perpendicular to a first portion. The first portion may be realized as a cylindrical rod. Furthermore, the second portion may have a rectangular cross-section. The locking member may be made of metal.

The torque-limiting assembly may further comprise at least one guiding structure for slidingly accommodating the at least one shearable piece. The guiding structure may have at least three support points for guiding the shearable piece in its longitudinal direction. The guiding structure may, for example, be realized as a canal (e.g., as a bore or groove). Moreover, the locking member may be slidingly accommodated in the at least one guiding structure (e.g., in the same guiding structure than the shearable piece or in a separate guiding structure).

Furthermore, the at least one guiding structure may extend substantially parallel with the longitudinal axis of the housing. According to one realization, the housing of the assembly comprises a first portion with a larger circumference about the longitudinal direction of the housing and a second portion with a smaller circumference about the longitudinal direction of the housing. The first portion may be constituted by a cylindrical portion. Furthermore, the first portion may have a polygonal portion at its outer circumference about the longitudinal axis. The second portion of the housing may be cylindrical.

The at least one guiding structure may be adapted to align with the at least one shear off structure. When for example the ring gear of a planetary gearing is turned to a position where it can receive a shearable piece (e.g., from the guiding structure) the at least one guiding structure is aligned with the at least one shear off structure. For example, a shearable piece slided in the at least one guiding structure is thereby also slided parallel to the shear off structure.

The torque-limiting assembly may further comprise a feeding mechanism for feeding the shearable piece towards the shear off structure. According to one realization, the feeding mechanism comprises a threaded portion, a feeding wheel engaged with the threaded portion and wherein the feeding wheel is adapted to engage the shearable piece. The threaded portion may be a portion of the outer surface of the housing of the assembly. The pitch of the thread may be 0.5 to 5 mm (e.g., 2 mm). The feeding wheel may longitudinally engage the locking member by rotation of the feeding wheel.

According to one realization, the feeding wheel comprises at least one haptic stop. Alternatively, a part rotationally fixed to the feeding wheel may comprise at least one haptic stop. The haptic stop may be a recess in the feeding wheel or in the part rotationally fixed to the feeding wheel for engagement of a portion of the locking member.

As an alternative, or additionally, the torque-limiting assembly may comprise a springingly biased feeding mechanism for pushing the locking member and/or the at least one shearable piece within the at least one guiding structure. The springingly biased feeding mechanism may be realized by at least one compression spring in each of the at least one guiding structure. Of course, there may exist still further feeding mechanisms.

The torque-limiting assembly may further comprise a reservoir for collecting sheared off material from the at least one shearable piece. Additionally, the reservoir may comprise a lid accessible from the exterior of the assembly.

In another variant, the two relatively rotatable parts may include the input shaft and the output shaft. The output shaft may have a hollow cylindrical portion at one end enclosing the input shaft or vice versa. Also in this variant, the torque-limiting assembly may further comprise at least one guiding structure for slidingly accommodating the at least one shearable piece. The guiding structure may be a bore in the input shaft and/or in the output shaft. Furthermore, the bore may be substantially perpendicular to the longitudinal direction of a part of the input or of a part of the output shaft. The bore may at least partially be conical.

In this variant, the shear off structure may be configured as a surface of the input shaft or of a part rotationally fixed to the input shaft. Alternatively, the shear off structure may be configured as a surface of the output shaft or of a part rotationally fixed to the output shaft. The surface may extend in the radial and the longitudinal direction of the input shaft or the output shaft.

According to a further aspect, there is provided a system comprising the torque-limiting assembly and at least one shearable piece wherein the shearable piece comprises a shearable material. The shearable piece may be brought into abutment with the shear off structure by a sliding movement in the guiding structure.

The at least one shearable piece may have a uniform tensile strength. Furthermore, the at least one shearable piece may be cylindrical. The at least one shearable piece may be solid. According to one realization, the at least one shearable piece is made of a polymer material.

The at least one shearable piece of the system may be colour-coded and the system may further comprise at least one colour-coded bone implant, wherein the at least one shearable piece and the at least one bone implant have the same colour-coding.

According to a still further aspect, there is provided a use of a shearable piece comprising a shearable material in a torque-limiting assembly for a surgical powertool. Also provided is a surgical powertool comprising the torque-limiting assembly presented herein. The surgical powertool may be configured as a surgical screwdriver, as a surgical drill or any other instrument for surgical purposes.

BRIEF DESCRIPTION OF THE DRAWINGS

Further details, advantages and aspects of the present disclosure will become apparent from the following embodiments taking in conjunction with the drawings, wherein.

DETAILED DESCRIPTION

In the following, various embodiments of a torque-limiting assembly, a system and a surgical powertool comprising the torque-limiting assembly will be described. The same reference numerals will be used to denote the same or similar structural features.

Figure 1:
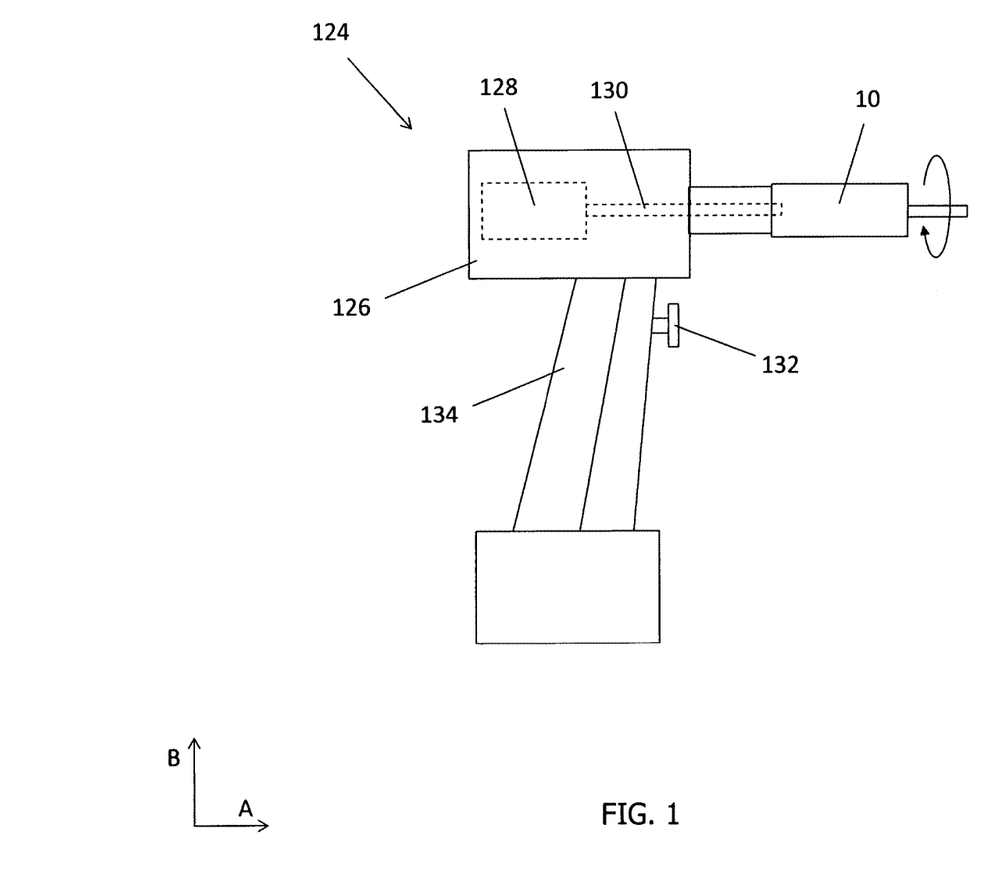
FIG. 1 shows a side view of a powertool comprising a torque-limiting assembly according to a first or second embodiment.

Throughout the description, a forward direction or front refers to the direction indicated by arrow A in FIG. 1 and a backward direction or rear refers to the opposite direction. Similarly, an upper direction refers to a direction indicated by arrow B in FIG. 1 and a lower direction refers to the opposite direction.

FIG. 1 shows a side view of an embodiment of a powertool 124, in particular a surgical powertool such as a surgical screwdriver, to which a torque-limiting assembly 10 of the present disclosure is removably attached. In other embodiments, the torque-limiting assembly 10 may be an integral part of the powertool 124.

The powertool 124 includes a casing 126 in which a motor 128 (shown in phantom) and a drive shaft 130 (shown in phantom) driven by the motor 128 are enclosed. Actuation of a trigger switch 132, mounted to a handle 134 connected to the casing 126, results in the actuation of the motor 128 and a rotation of the drive shaft 130.

Figure 2:
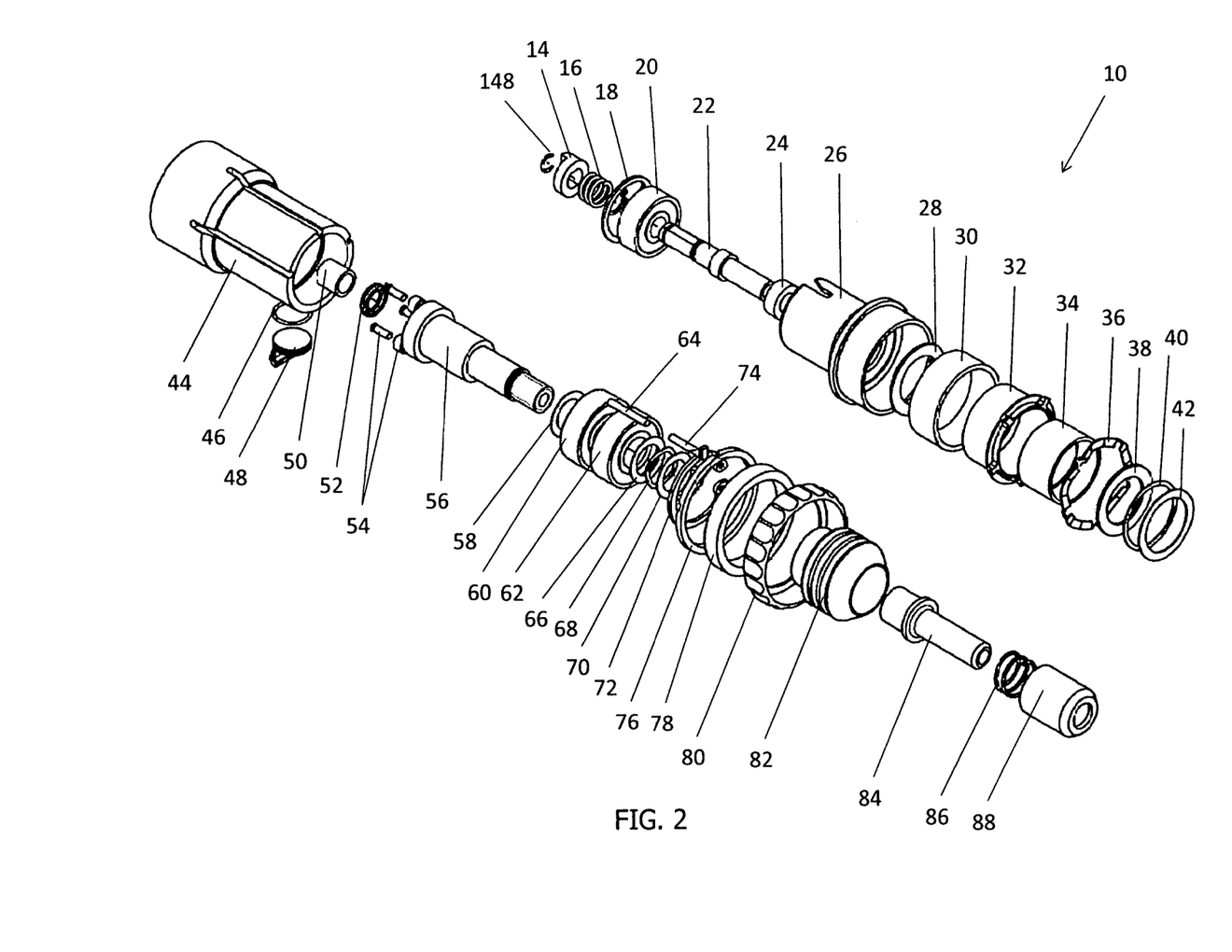
FIG. 2 shows an exploded view of the torque-limiting assembly of the first embodiment.
Figure 3:
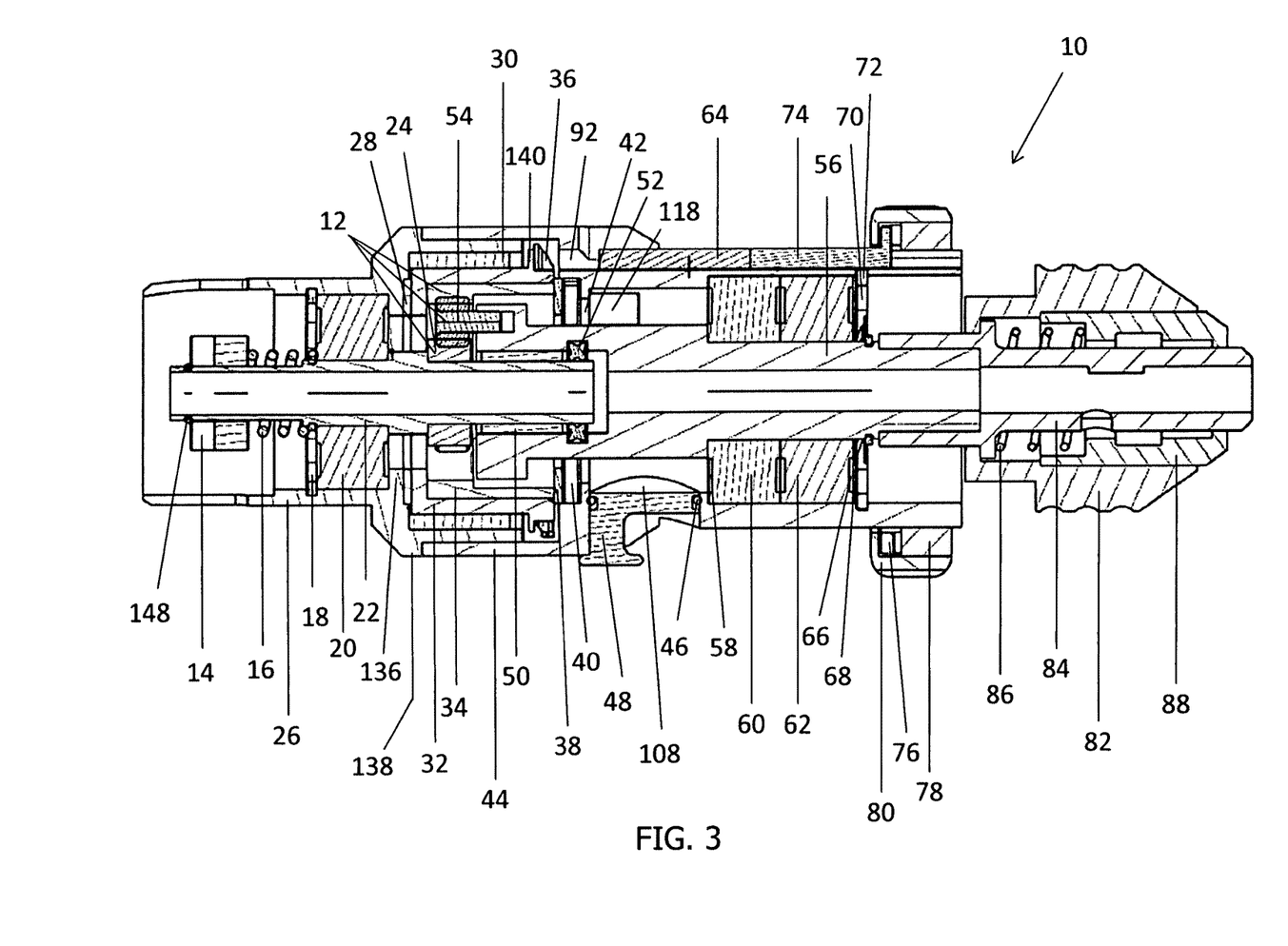
FIG. 3 shows a cross-sectional view of the torque-limiting assembly of the first embodiment.

With reference to FIGS. 2 and 3, the torque-limiting assembly 10 comprises in one embodiment an input shaft 22 adapted to be rotationally driven by the drive shaft 130 of the powertool 124. A retaining ring 148 is fitted around the input shaft 22 adjacent to its rear end. The retaining ring 148 is fitted in an angular groove formed in a circumference of the input shaft 22 and prevents a dog clutch 14 from sliding off the input shaft 22.

The input shaft 22 has a circumferential first portion at its rear end comprising two opposing circular surfaces and two opposing flat surfaces. The dog clutch 14 is slidingly engaged along this first portion of the input shaft 22. The inner circumference of the dog clutch 14 mates with the outer circumference of the first portion of the input shaft 22. In other words, the inner circumference of the dog clutch 14 also includes two opposing circular surfaces and two opposing flat surfaces. When connecting the torque-limiting assembly 10 to the powertool 124, the dog clutch 14 is engaged by a corresponding dog clutch (not shown) connected to the drive shaft 130.

The input shaft 22 is rotatably held in an adapter 26 by a rear bearing assembly 20. The adapter 26 comprises a rear cylindrical portion and a front cylindrical portion. A washer 18 is placed in a recess along an inner circumference of the rear cylindrical portion of the adapter 26. The rear bearing assembly 20 is longitudinally fixed between the washer 18 and an abutment 136 of the adapter 26 which abuts radially and inwardly between the front and rear cylindrical portions of the adapter 26. The dog clutch 14 is springingly biased backwards against the retaining ring 148 by a spring 16 between the dog clutch 14 and the rear bearing assembly 20. The spring 16 is a helical compression spring and encloses the input shaft 22.

The rear cylindrical portion of the adapter 26 encloses the rear part of the input shaft 22, the retaining ring 148, the dog clutch 14, the spring 16, the washer 18 and the rear bearing assembly 20. The front cylindrical portion of the adapter 26 has a larger diameter than the diameter of the rear cylindrical portion. The abutment 136 is located longitudinally between the rear cylindrical portion and the front cylindrical portion of the adapter 26. Furthermore, the adapter 26 has a radially outwardly protruding collar 138 which extends from the front cylindrical portion of the adapter 26.

A washer 28 is inserted in a circular recess in the front part of the abutment 136. A ring gear bearing 30 has an outer diameter which corresponds to the inner diameter of the front cylindrical portion of the adapter 26. The outer portion of the ring gear bearing 30 is connected to the inside of the front cylindrical portion of the adapter 26.

A sleeve 32 is connected to the inner portion of the ring gear bearing 30. The sleeve 32 has a radially inwardly protruding collar at its rear end which abuts against the washer 28. The sleeve 32 further comprises a radially outwardly protruding collar 140 adjacent to its front end. A washer 36 is coupled around the front end of the sleeve 32 and abuts against the collar 140.

A ring gear 34 of a planetary gearing 12 is fixed to the inner circumference of the sleeve 32. The sleeve 32 and the ring gear 34 may thereby rotate relative to the adapter 26. A sun gear 24 of the planetary gearing 12 is connected to the input shaft 22. A sealing 52 is arranged around the front end of the input shaft 22. Between the sun gear 24 and the sealing 52, a bearing 50 is provided.

An output shaft 56 is rotationally coupled with the input shaft 22 by the bearing 50. The output shaft 56 is generally cylindrical and has a larger inner diameter portion at its rear end and a smaller inner diameter portion at its front end. A circular recess is provided along the larger inner diameter portion of the output shaft 56 for accommodating the sealing 52. The rear end of the output shaft 56 comprises a planet carrier of the planetary gearing. Three planet gears 54 can be seen in FIG. 2 (only one is visible in FIG. 3) which are rotationally coupled to the planet carrier of the output shaft 56. The planet gears 54 can rotate about the longitudinal direction relative to the output shaft 56. The planetary gearing 12 according to this configuration generates a higher torque and a slower rotational speed of the output shaft 56 relative to the input shaft 22.

A housing 44 of the assembly is connected to the outer surface of the front cylindrical portion of the adapter 26. The housing 44 abuts against the collar 138 of the adapter 26. The housing 44 comprises two cylindrical portions, a rear cylindrical portion having a larger diameter and a front cylindrical portion having a smaller diameter. Furthermore, the housing 44 comprises a radially inwardly protruding collar adjacent to the rear end of the smaller diameter portion. The radially inwardly protruding collar of the housing 44 is spaced apart in the longitudinal direction from the ring gear 34 and the sleeve 32 by two washers 38 and 40. Moreover, the radially inwardly protruding collar of the housing 44 radially encloses a washer 42 between the output shaft 56 and the housing 44.

The output shaft 56 is rotatably connected to the housing 44 via a front bearing assembly comprising two bearings 60 and 62. The bearing 60 abuts against an edge around the inner circumference of the housing 44 and an edge around the outer circumference of the output shaft 56. A washer 58 is provided to the rear surface of bearing 60 and a washer 66 is provided at the front end of the bearing 62. A wave spring 68 is provided in front of the washer 66 and is compressed in its longitudinal direction by a washer 70 and a retaining ring 72. The retaining ring 72 is accommodated in a recess along the inner circumference of the housing 44. The retaining ring 72 thereby holds the washer 70.

Three guiding structures 92 are formed in the upper part of the housing 44 in the longitudinal direction (only one guiding structure at the top can be seen in FIG. 3). The guiding structures 92 are here realized as grooves extending along the outer surface of the smaller diameter portion and through the inner surface of the housing 44. The ring gear 34, the sleeve 32 and the washer 36 are in a rotational position in which a surface of the washer 36, parallel with the longitudinal direction of the housing 44, is aligned with the top guiding structure 92. That is, a surface of the washer 36 tangents the guiding structure 92 in the circumferential direction but the washer 36 and the guiding structure 92 are spaced apart in the longitudinal direction. As will be described later in more detail, this surface of the washer 36 functions as a shear off structure.

A shearable piece 64 of a round cylindrical shape and made from a polymer material is slidingly accommodated in the guiding structure 92. The shearable piece 64 is adapted to slide in a backward direction until it abuts against the washer 36. When the sleeve 32, the ring gear 34 and the washer 36 are aligned with the guiding structure 92, the shearable piece 64 abuts against the shear off structure of the washer 36 in a circumferential direction. The shear off structure is thereby parallel with the longitudinal extension of the shearable piece 64.

The housing 44 comprises a threaded portion on the outer circumference of the smaller diameter portion. A feeding wheel 80 is engaged with the threaded portion. The feeding wheel 80 is circular and has a radially inwardly protruding collar at its rear end. A ring 78 is connected to the inner circumference of the feeding wheel 80 spaced apart from the collar in the longitudinal direction. A feeding wheel washer 76 abuts against the rear end of the ring 78 inside the feeding wheel 80. A clearance is established in the longitudinal direction between the collar of the feeding wheel 80 and the feeding wheel washer 76.

A locking member 74 is provided that has a cylindrical portion slidingly accommodated in the guiding structure 92. The locking member 74 has an L-shape. A portion of the locking member 74 perpendicular to the cylindrical portion of the locking member 74 is accommodated in the clearance between the collar of the feeding wheel 80 and the feeding wheel washer 76. Rotation of the feeding wheel 80 causes the locking member 74 to move along the guiding structure 92. Rotation of the feeding wheel 80 in one direction causes the feeding wheel washer 76 to push the locking member 74 backwards. Rotation of the feeding wheel 80 in the opposite direction causes the collar of the feeding wheel 80 to pull the locking member 74 forward.

A drive spindle 84 of a keyless drill chuck is connected to the front end of the output shaft 56. The keyless drill chuck comprises a spring 86, the drive spindle 84, a chuck head 82 and an adapter 88. The drive spindle 84 has a rear cylindrical portion which is coupled with the outer circumference of the front end of the output shaft 56. The drive spindle 84 further has a slightly cone shaped portion at its front end and a radially outwardly protruding collar is arranged between the rear cylindrical portion and the front cone shaped portion. The cone shaped portion of the drive spindle 84 is flexible in its radial direction. Furthermore, the cone shaped portion has a smaller outer diameter closer to the radially outwardly protruding collar and a larger outer diameter closer to its front end. The adapter 88 has a cylindrical outer surface and is connected to the inside of the chuck head 82.

The chuck head 82 has a radially inwardly protruding portion at its rear end slidingly engaged with the rear cylindrical portion of the drive spindle 84. The spring 86 is a compression spring which acts between the radially outwardly protruding collar of the drive spindle 84 and a radially inwardly protruding portion of the adapter 88. The spring 86 thereby pushes the radially inwardly protruding portion of the chuck head 82 against the collar of the drive spindle 84 via the chuck head 82.

The adapter 88 has a radially inwardly protruding portion at its front end in sliding contact with the conical outer surface of the drive spindle 84. In the situation illustrated in FIG. 3, the front portion of the drive spindle 84 is compressed by the radially inwardly protruding portion of the adapter 88. The drive spindle 84 further comprises a cylindrical bore along its longitudinal direction and a protrusion at the inner surface of the bore.

By pulling the chuck head 82 backwards, the front portion of the drive spindle 84 will slightly expand and a bit for screwing can be inserted into the drive spindle 84. When releasing the chuck head 82, the spring will urge the chuck head 82 and the adapter 88 forward. The radially inwardly protruding portion at the front of the adapter 88 will thereby compress the front portion of the drive spindle 84 and the protrusion at the inner surface can be engaged with the bit. The bit is thereby fixed to the output shaft 56.

In the situation illustrated in FIG. 3, the ring gear 34, the sleeve 32 and the washer 36 are freely rotatable relative to the housing 44. The planetary gearing 12 is thereby not adapted to transmit any (substantial) torque from the input shaft 22 to the output shaft 56.

By rotating the feeding wheel 80 in one direction, the shearable piece 64 is pushed by the locking member 74 and thereby slides backwards in the guiding structure 92 until it abuts against the washer 36. The ring gear 34, the sleeve 32 and the washer 36 are thereby rotationally locked relative to the housing 44 by the shearable piece 64. When the input shaft 22 is rotated, the sun gear 24 and the stationary ring gear 34 will mesh with the planet gears 54 which will be driven around the sun gear 24. The planet gears 54 will thereby rotate the planet carrier at the rear end of the output shaft 56 and a torque will consequently be transmitted from the input shaft 22 to the output shaft 56.

When the torque acting on the input shaft 22 increases, a force acting on the shearable piece 64 perpendicular to its longitudinal direction by the shear off structure of the washer 36 will also increase. When the force becomes sufficiently large and exceeds a predefined torque limit, the shearable piece 64 will be sheared off between the washer 36 and the guiding structure 92. The torque acting upon the sleeve 32, the ring gear 34 and the washer 36 upon breaking of the shearable piece 64 is defined as a torque limit. One or two additional shearable pieces 64 may be inserted in the two remaining guiding structures 92 and engaged with the ring gear 34 in the same manner. The torque limit may consequently be increased (e.g., doubled or tripled). In other embodiments, shearable pieces 64 of different diameters or different tensile strengths may be used and combined to selectively define and adjust the torque limit.

When the shearable piece 64 has broken, the sleeve 32, the ring gear 34 and the washer 36 are again substantially freely rotatable relative to the housing 44, and (substantially) no torque will be transmitted to the output shaft 56 upon further rotation of the input shaft 22.

The remainder of the shearable piece 64 in the guiding structure 92 may be used again to rotationally lock the ring gear 34 relative to the housing 44 by further rotating the feeding wheel 80. The rotation of the feeding wheel 80 pushes the remainder of the shearable piece 64 by the locking member 74 in the guiding structure 92 until it abuts against the washer 36 as described above.

The sheared off part of the shearable piece 64 can be collected in a reservoir 108. The reservoir 108 is closed with a lid 48 comprising a sealing ring 46. Two openings 118 (see also FIGS. 7A-7D) are arranged in the housing 44 for guiding sheared off material of the shearable piece 64 to the reservoir 108. The reservoir 108 prevents the sheared off material to come into contact with the patient.

When the entire length of the shearable piece 64 has been used or when the shearable piece 64 is removed from the guiding structure 92, the locking member 74 may be used to rotationally lock the ring gear 34 relative to the housing 44. The locking member 74 may be pushed backwards in the guiding structure 92 until it abuts against the washer 36 by rotating the feeding wheel 80 as previously described. The locking member 74 may be made from metal and has a higher tensile strength than the shearable piece 64. Consequently, by rotationally lock the washer 36, the ring gear 34 and the sleeve 32 relative to the housing 44 by the locking member 74, a higher torque may be transmitted from the input shaft 22 to the output shaft 56. The locking member 74 is not adapted to be sheared off by the shear off structure of the washer 36.

Following this operation, the locking member 74 may be pulled forward by rotating the feeding wheel 80 in the opposite direction and a new shearable piece 64 may again be inserted in the guiding structure 92 and the above described procedure can be repeated.

Figure 4:
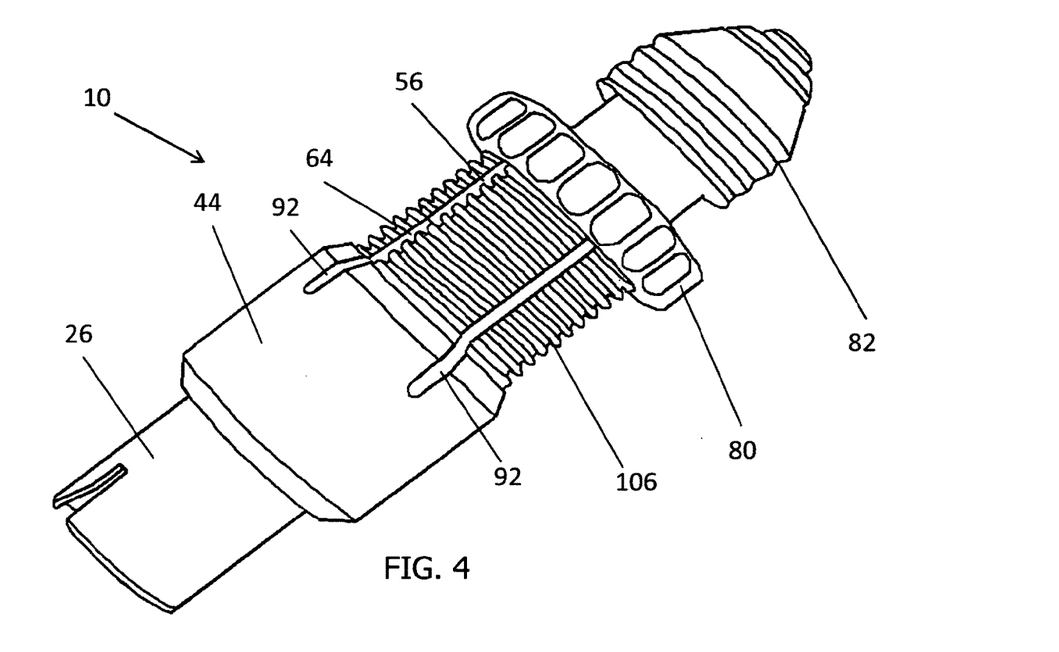
FIG. 4 shows a perspective view of the torque-limiting assembly of FIG. 3.

FIG. 4 shows a perspective view of the torque-limiting assembly 10. The housing 44 comprises the three guiding structures 92 of which two can be seen in FIG. 4. The shearable piece 64 and the locking member 74 do not radially extend outside the threads of the threaded portion 106 of the housing 44. The chuck head 82 at the front end of the torque-limiting assembly 10 comprises three circumferential notches for providing a better grip to the operator. The feeding wheel 80, engaged with the threaded portion 106, is also provided with notches around its outer circumference.

Figure 5:
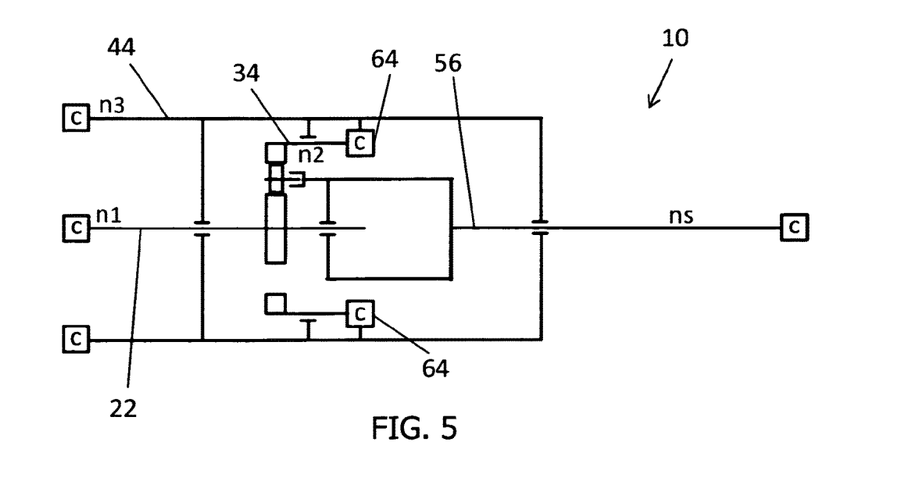
FIG. 5 shows a schematic functional view of the torque-limiting assembly of FIG. 3.

FIG. 5 schematically illustrates rotations of parts of the torque-limiting assembly 10. In this illustrated situation, two shearable pieces 64 are shown. The rotating speed of the input shaft 22 is denoted n1. n2 denotes the rotating speed of the ring gear 34, n3 the rotation of the housing 44 (which is stationary) and ns the rotation of the output shaft 56. When the ring gear 34 and the housing 44 are rotationally locked by the two shearable pieces 64 (or by the locking member 74), the rotation of the input shaft 22 is transmitted to the output shaft 56 via the planetary gearing 12. The rotating speed of the output shaft 56 relative to the input shaft 22 depends on the ratio of the planetary gearing 12. In the present embodiment, a planetary gearing 12 with a ratio of 3:25:1 may be used.

If the ring gear 34 is rotationally locked relative to the housing 44 (n2 is equal to n3) with the two shearable pieces 64, a maximum torque that can be transmitted from the input shaft 22 to the output shaft 56 is defined by the tensile strength of the shearable pieces 64. When exceeding this torque, the shearable pieces 64 will shear off and the ring gear 34 is then rotatable relative to the housing 44 (if one of the shearable pieces 64 shears off before the other, the torque acting on the remaining shearable piece 64 will practically be doubled and the remaining shearable piece 64 will therefore immediately also be sheared off). The rotation of the input shaft 22 will thereby only result in a rotation of the ring gear 34 (n2 is not equal to n3).

The denotation c at the rear end of the torque-limiting assembly 10 denotes the coupling between the adapter 26 and the powertool 124. The denotation c between the ring gear 34 and the housing 44 schematically illustrates the coupling function of the two shearable pieces 64. Additionally, the denotation c at the front end of the keyless drill chuck, schematically illustrates the coupling between the drive spindle 84 and the bit (not shown).

Figure 6A:
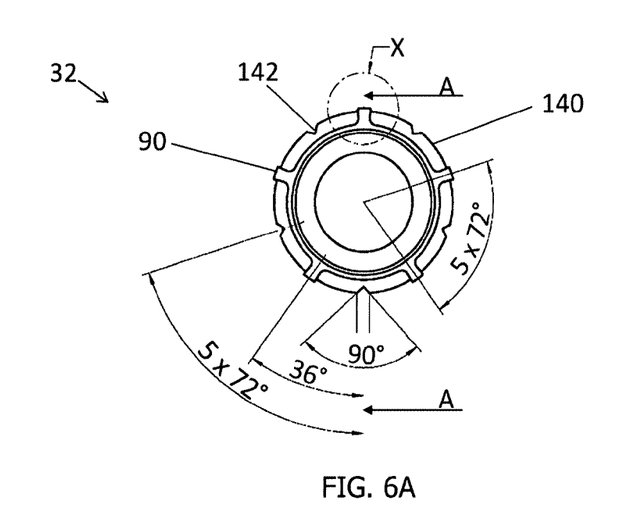
FIGS. 6A-6D shows a front view, a cross-sectional view, a perspective view and an enlarged view of a sleeve of the torque-limiting assembly of FIG. 3.

FIGS. 6A to 6D illustrate different views of the sleeve 32 which is rotationally coupled with the ring gear 34 in FIG. 3. FIG. 6A illustrates a front view of the sleeve 32 where five shear off structures 90 are equally spaced along the circumference of the sleeve 32. The sleeve 32 may be used in the torque-limiting assembly 10 with or without the washer 36 (not shown). The sleeve 32 further comprises five cuts 142 at the collar 140, each between two of the five shear off structures 90.

Figure 6B:
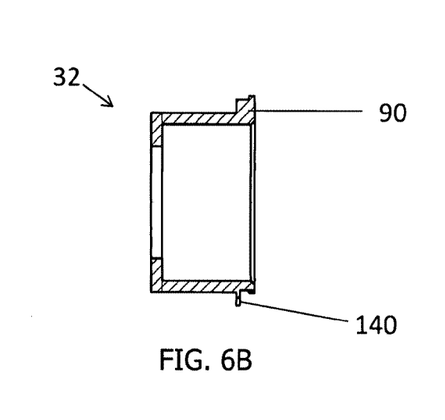

FIG. 6B illustrates a cross-section along line A-A of FIG. 6B. Here, the radially inwardly protruding collar can be seen at the rear end of the sleeve 32. The collar defines an opening for accommodating the input shaft 22 (not shown). The collar is spaced approximately 2 mm in the longitudinal direction from the front end of the sleeve 32.

Figure 6C:
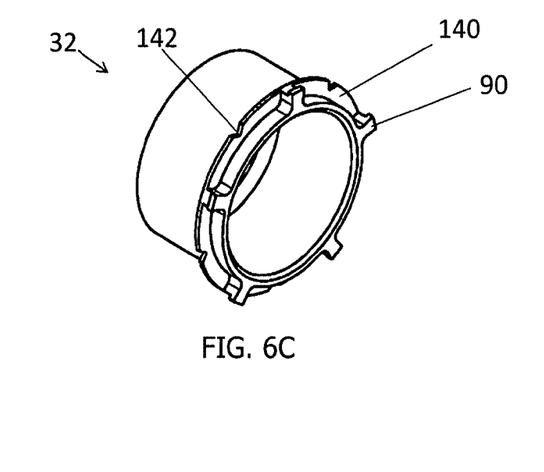

FIG. 6C illustrates a perspective view of the sleeve 32. The shear off structures 90 may have a length in the longitudinal direction between 1 to 5 mm (e.g., of 2 mm).

Figure 6D:
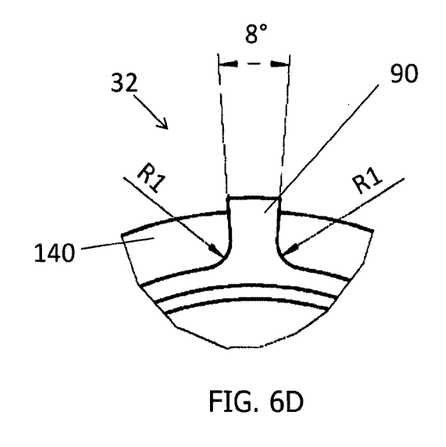

FIG. 6D illustrates an enlarged view of the area X in FIG. 6A. The angular relationship between the two opposing radial surfaces is 8 degrees. The two opposing surfaces are both extending in the longitudinal direction. As an alternative, one of the two opposing surfaces may be slightly inclined relative to the longitudinal direction toward the second surface. Consequently, the two surfaces thereby adapt a wedge shape. One of the surfaces of the shear off structures 90 can thereby be used for shearing off material from shearable pieces 64 and the second surface can function as a guiding surface for guiding sheared off material to the reservoir 108 via the openings 118 of the housing 44.

Figure 7A:
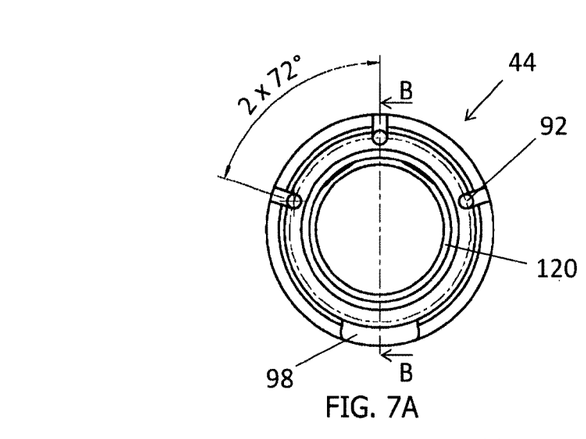
FIGS. 7A-7D shows a front view, a cross-sectional view, a rear view and a perspective view of a housing of the torque-limiting assembly of FIG. 3.

FIGS. 7A to 7D illustrate four different views of the housing 44. FIG. 7A illustrates a front view of the housing 44 comprising the three guiding structures 92 realized as three grooves. One guiding structure 92 is arranged at the top of the housing 44 and each of the two remaining guiding structures 92 is spaced from the top guiding structure 92 at an angular distance of 72 degrees. At the lower portion of the housing 44, an opening 98 can be seen into which the lid 48 with its sealing ring 46 may be introduced to close the reservoir 108.

Figure 7B:
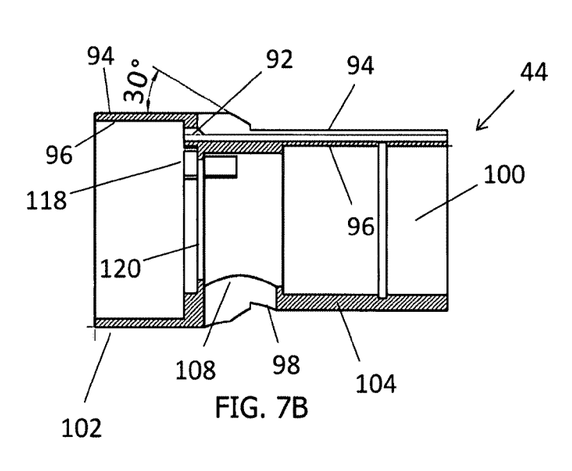

FIG. 7B illustrates a cross section along line B-B of FIG. 7A. A larger diameter portion 102 is arranged at the rear side of the housing 44 and a smaller diameter portion 104 is arranged at the front side of the housing 44. A transition portion is arranged between the larger diameter portion 102 and the smaller diameter portion 104. One surface of the transition portion is inclined 30 degrees with respect to the longitudinal axis 100 of the housing 44. The housing 44 has an inner surface 96 and an outer surface 94. Moreover, the guiding structure 92 extends between the outer surface 94 and the inner surface 96 of the housing 44. The housing 44 has a radially inwardly protruding collar 120 which defines the smallest inner diameter of the housing 44. Two openings 118 (only one can be seen in FIG. 7B) are provided in a longitudinal direction through the collar 120. The openings 118 define a communication between the larger diameter portion 102 and the reservoir 108 radially outside of the inner edge of the collar 120.

Figure 7C:
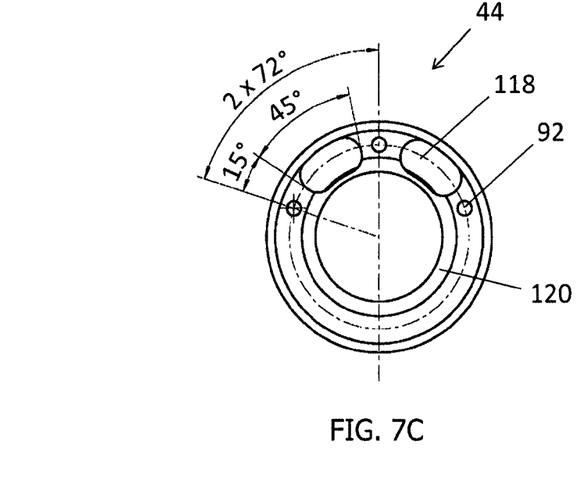

FIG. 7C shows a rear view of the housing 44. Here, both openings 118 can been seen. The two openings 118 are positioned between the three guiding structures 92 in the circumferential direction. The openings 118 have an elongated shape with an angular extension of 45 degrees. The center of the openings 118 have approximately the same distance in the radial direction to the center of the housing 44 as the distance between the guiding structure 92 and the center of the housing 44. In this illustrated view, it can further be seen that the inner edge of the collar 120 is continuous along its inner circumference.

Figure 7D:
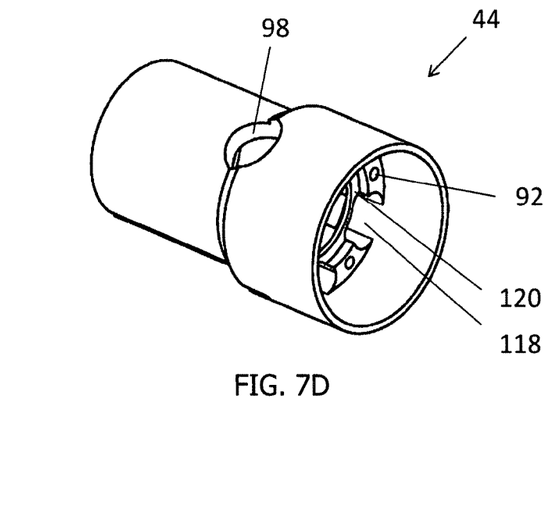

FIG. 7D shows a perspective view of the housing 44 wherein the two openings 118 (one of the openings is partly hidden) can be seen from the rear side of the housing 44. From this figure, it may further be seen that the opening 98 into the reservoir 108 is realized as a circular bore between the outer surface 94 and the inner surface 96 of the housing 44 at a transition portion between the larger diameter portion 102 and the smaller diameter portion 104.

Figure 8:
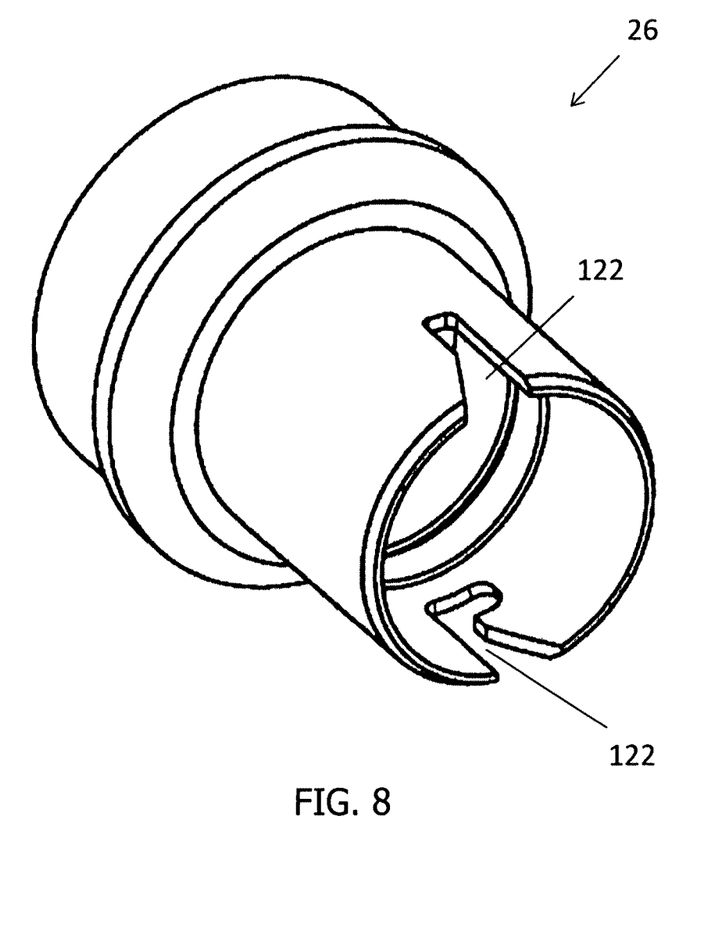
FIG. 8 shows a perspective view of an adapter of the torque-limiting assembly of FIG. 3.

FIG. 8 shows a rear perspective view of the adapter 26. The rear cylindrical portion of the adapter 26 comprises two diagonally opposing slots 122. The two slots 122 each have a portion extending in the longitudinal direction of the adapter 26. One of the slots 122 has a further portion substantially perpendicular to the portion extending in the longitudinal direction. However, both slots 122 may comprise such a perpendicular portion. The powertool 124 may have a cylindrical portion of the casing 126 with a radially outwardly protruding pin. The adapter 26 may thereby be connected to the powertool 124 by longitudinally moving the adapter 26 so that the pin engages the longitudinal portion of the slot 122. Subsequently, the adapter 26 may be turned in order to engage the pin with the perpendicular portion of the slot 122. The adapter 26 is thereby fixed to the powertool 124.

Figure 9A:
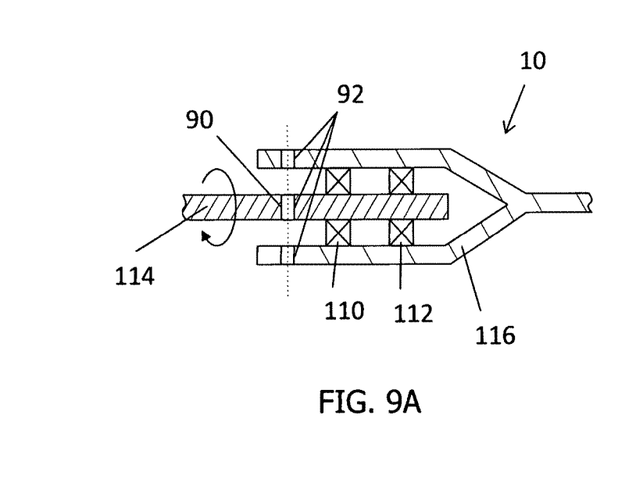
FIGS. 9A-9D shows three cross-sectional views and one side view of a torque-limiting assembly according to the second embodiment.

FIGS. 9A to 9D show a torque-limiting assembly 10 according to a second embodiment. FIG. 9A shows a cross-sectional view of the torque-limiting assembly 10 comprising an input shaft 114 coupled to an output shaft 116 via two bearings 110 and 112. The input shaft 114 may thereby rotate relative to the output shaft 116. The output shaft 116 has a cylindrical portion covering the bearings 110 and 112 and a part of the input shaft 114. The torque-limiting assembly 10 comprises a guiding structure 92. Here, the guiding structure 92 is realized as a bore through the cylindrical portion of the output shaft 116 and the input shaft 114. The torque-limiting assembly 10 may comprise a plurality of longitudinally spaced guiding structures 92. The bore through the input shaft 114 forms a shear off structure 90 for shearing off a shearable piece 64. The bore may be slightly conical. In FIG. 9A, no rotational movement of the input shaft 114 will be transmitted to the output shaft 116. The input shaft 114 and the output shaft 116 are consequently two relatively rotatable parts of the torque-limiting assembly 10.

Figure 9B:
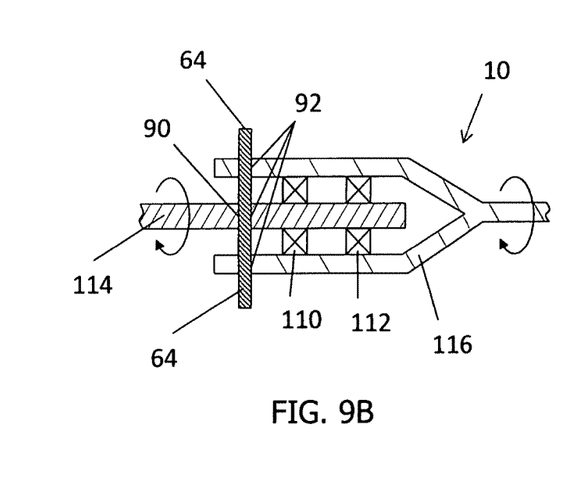

FIG. 9B shows a torque-limiting assembly 10 according to FIG. 9A but where a shearable piece 64 has been inserted into the guiding structure 92. In this illustrated situation, the rotational movement of the input shaft 114 will be transmitted to the output shaft 116.

Figure 9C:
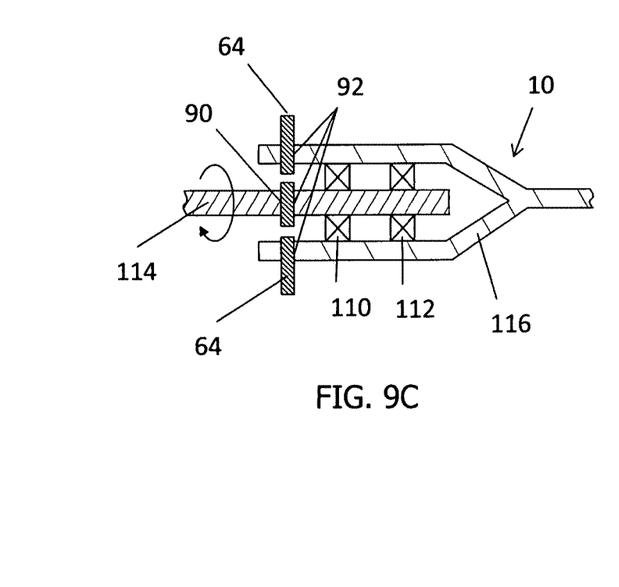

FIG. 9C shows the torque-limiting assembly 10 according to FIG. 9B but where the torque acting between the input shaft 114 and the output shaft 116 has exceeded a torque limit. As can be seen from the figure, the shearable piece 64 has been sheared off by shear off structure 90. In this illustrated situation, no torque can be transmitted from the input shaft 114 to the output shaft 116.

Figure 9D:
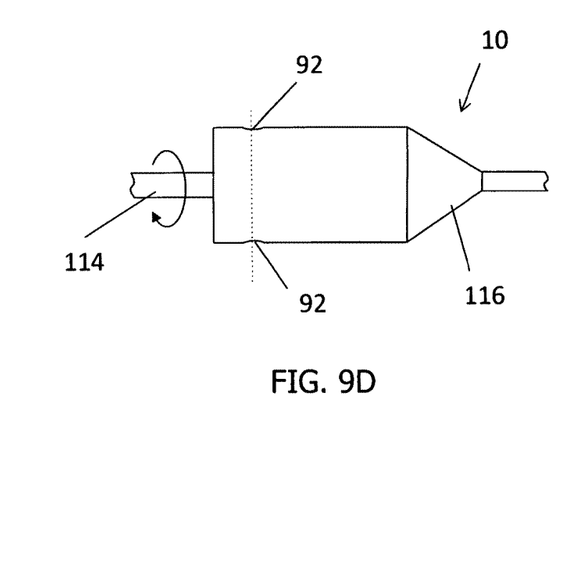

FIG. 9D shows a side view of the torque-limiting assembly 10 as illustrated in FIG. 9A. The openings of the guiding structure 92 are slightly visible at the top and bottom part of the cylindrical portion of the output shaft 116.

A keyless drill chuck of the first embodiment may be coupled to the output shaft 116 of the torque-limiting assembly 10 according to the second embodiment. Furthermore, the input shaft 114 may be coupled directly to the drive shaft 130 of the powertool 124. A mechanical torque-limiting function can thereby be easily implemented into an existing powertool 124.

Figure 10:
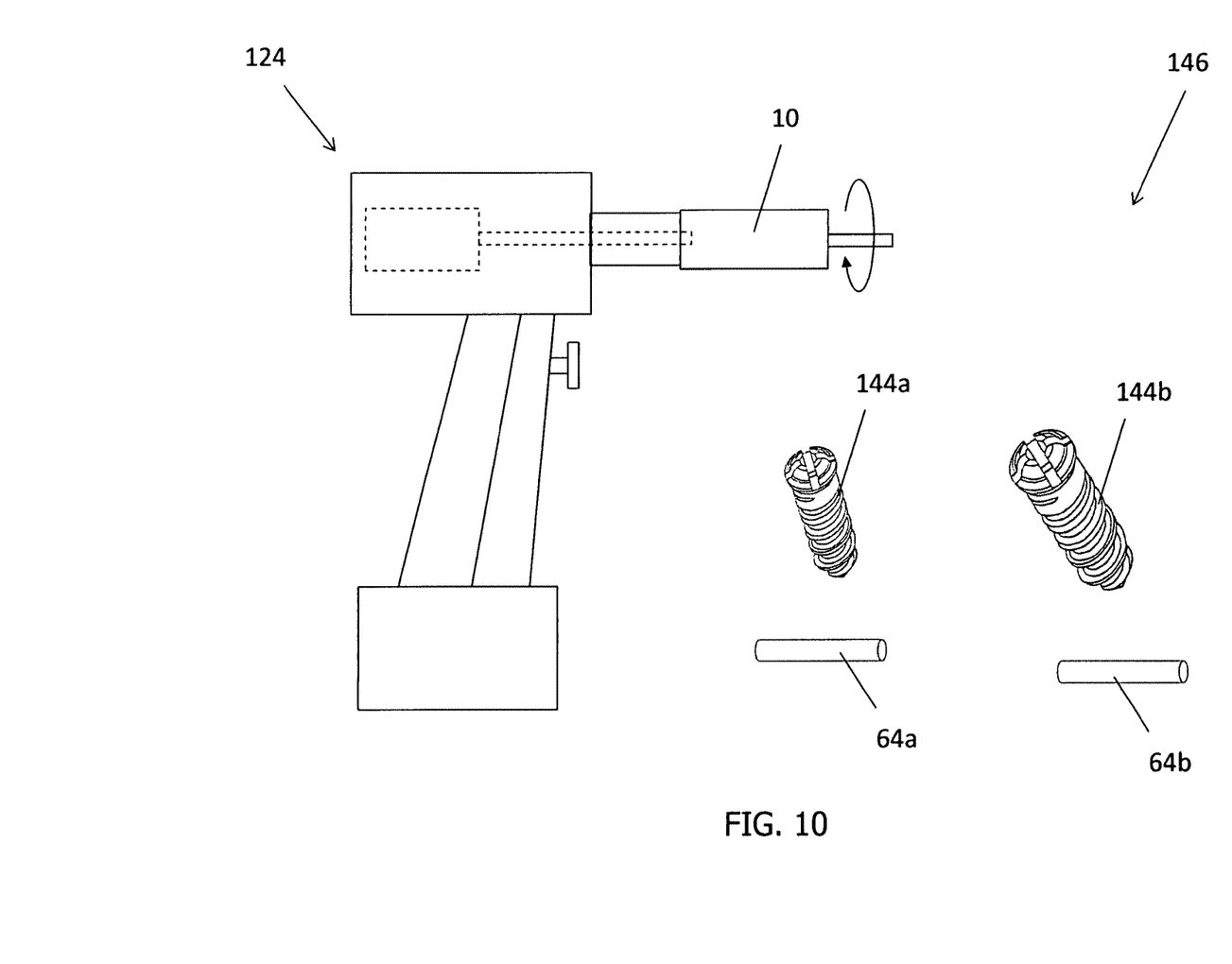
FIG. 10 shows a system comprising a powertool with a torque-limiting assembly according to the first or second embodiment.

FIG. 10 shows a system 146 comprising the powertool 124 with a torque-limiting assembly 10 according to the first or second embodiment. The system 146 further comprises two bone implants 144 and two shearable pieces 64. The bone implants 144 may be bone screws. The two bone implants 144 are designed for differently applied screwing torques. The two shearable pieces 64a and 64b define the designated torque limits for the first and second bone implants 144a and 144b, respectively, when used in the torque-limiting assembly 10. Therefore, the bone implant 144a and the shearable piece 64a are colour-coded with a first colour and the bone implant 144b and the shearable piece 64b are colour-coded with a second colour, different from the first colour. The shearable pieces can be delivered sterile packed with a label which guarantees the proper torque limit.

During surgery, when a surgeon selects a bone implant 144 to be screwed into a bone of the patient, the surgeon can easily select a corresponding shearable piece 64 which is colour-coded with the same colour as the bone implant 144. The surgeon does thereby not need to estimate or look up the appropriate torque to be applied to the bone implant 144. Neither does the surgeon need to manually set the maximum screwing torque. The surgeon simply inserts a shearable piece 64, colour-coded with the same colour as the bone implant 144, into the guiding structure 92 of the torque-limiting assembly 10 and rotates the feeding wheel 80. This measure results in a faster surgical procedure and an insurance that a correct amount of torque will be applied to the bone implant 144.

When the surgeon wants to screw a plurality of bone implants 144 into bone with the same applied torque, the surgeon simply rotates the feeding wheel 80 between each screwing operation. A torque-limiting assembly 10 according to this disclosure does not need any recalibration since the properties of the shearable pieces 64 guarantee correctly defined torque limits. After surgery, the surgeon may empty the reservoir 108 by removing the lid 48 and can thereby let the sheared off material from the shearable pieces 64 be disposed as non-sterile waste.

While the present disclosure has been described with reference to exemplary embodiments, it will be appreciated that the present invention is not limited to what have been described above. For example, it will be appreciate that the dimensions of the parts may be varied as needed. Accordingly, it is intended that the present invention may be limited only by the scope of the claims appended hereto.

The invention claimed is:

1. A torque-limiting assembly for a surgical powertool, the assembly comprising:
    an input shaft and an output shaft, wherein two relatively rotatable parts of the assembly are configured to be locked against relative rotation by at least one shearable piece for torque transfer between the input shaft and the output shaft up to a torque limit;
    at least one shear off structure rotationally fixed to one of the two relatively rotatable parts for shearing off a portion of the at least one shearable piece above the torque limit so as to unlock the two relatively rotatable parts for relative rotation;
    a feeding mechanism for feeding the shearable piece towards the shear off structure; and
    a planetary gearing arranged between the input shaft and the output shaft,
    wherein the two relatively rotatable parts include:
        a stationary part of the torque-limiting assembly; and
        a part of the planetary gearing,
    wherein the planetary gearing includes a ring gear and wherein the shear off structure is rotationally fixed to the ring gear or to a part rotationally fixed to the ring gear.

2. The torque-limiting assembly according to claim 1, wherein the assembly further comprises a locking member for rotationally locking the two relatively rotatable parts above the torque limit.

3. The torque-limiting assembly according to claim 1, wherein the assembly further comprises at least one guiding structure for slidingly accommodating the at least one shearable piece.

4. The torque-limiting assembly according to claim 3, wherein the at least one guiding structure is adapted to align with the at least one shear off structure.

5. The torque-limiting assembly according to claim 3, wherein a locking member is slidingly accommodated in the at least one guiding structure.

6. The torque-limiting assembly according to claim 1, wherein the feeding mechanism comprises a threaded portion, a feeding wheel engaged with the threaded portion and wherein the feeding wheel is adapted to engage the shearable piece.

7. The torque-limiting assembly according to claim 1, wherein the assembly further comprises a reservoir for collecting sheared off material from the at least one shearable piece.

8. The torque-limiting assembly according to claim 7, wherein the reservoir comprises a lid accessible from the exterior of the assembly.

9. The torque-limiting assembly according to claim 1, wherein the two relatively rotatable parts include the input shaft and the output shaft.

10. The torque-limiting assembly according to claim 9, wherein the assembly further comprises at least one guiding structure for slidingly accommodating the at least one shearable piece.

11. The torque-limiting assembly according to claim 9, wherein the shear off structure is configured as a surface of the input shaft or of a part rotationally fixed to the input shaft.

12. The system according to claim 1, wherein the at least one shearable piece is color-coded and wherein the system further comprises at least one color-coded bone implant, wherein the at least one shearable piece and the at least one bone implant have the same color-coding.

13. A surgical powertool comprising the torque-limiting assembly according to claim 1.

14. A torque-limiting assembly for a surgical powertool, the assembly comprising:
an input shaft and an output shaft, wherein a first part and a second part of the assembly are relatively rotatable and are located between the input and output shaft and are configured to be locked against relative rotation up to a torque limit by the engagement of an elongate shearable piece mounted on the first rotatable part and a shearing structure mounted on the second part, the shearing structure capable of shearing off a portion of the shearable piece at a torque limit, the sheared off portion of the shearable piece being less than an entire length of the shearable piece;
a feeding mechanism for feeding a non-sheared off portion of the shearable piece into engagement with the shearing structure after the torque limit has been exceeded and the portion of shearable piece has been sheared off; and
a planetary gearing arranged between the input shaft and the output shaft,
wherein the two relatively rotatable parts include:
a stationary part of the torque-limiting assembly; and
a part of the planetary gearing,
wherein the planetary gearing includes a ring gear and wherein the shear off structure is rotationally fixed to the ring gear or to a part rotationally fixed to the ring gear.

15. The torque-limiting assembly according to claim 14, further comprising a housing, the feeding mechanism comprises a threaded portion on the housing, a feeding wheel threadably engaged with the threaded portion on the housing and wherein the feeding wheel is adapted to engage the shearable piece.

16. The torque-limiting assembly according to claim 14, wherein the assembly further comprises a reservoir for collecting the sheared off portion of the shearable piece for moving the shearable piece towards the shearing structure.

17. The torque-limiting assembly according to claim 14, wherein the assembly further comprises a locking member for rotationally locking the two relatively rotatable parts above the torque limit.

* * * * *